United States Patent
Carpenter et al.

(10) Patent No.: US 8,798,963 B2
(45) Date of Patent: Aug. 5, 2014

(54) CONTAINER TRANSPORT MONITORING AND ANALYSIS

(75) Inventors: Michael D. Carpenter, Arlington, TX (US); Svetlozar Delianski, Berlin (DE); Matthias Krause, Orsingen-Nenzingen (DE)

(73) Assignee: Siemens Industry, Inc., Alpharetta, GA (US)

( * ) Notice: Subject to any disclaimer, the term of this patent is extended or adjusted under 35 U.S.C. 154(b) by 714 days.

(21) Appl. No.: 13/075,281

(22) Filed: Mar. 30, 2011

(65) Prior Publication Data

US 2011/0231158 A1    Sep. 22, 2011

Related U.S. Application Data (63) Continuation-in-part of application No. 12/802,392, filed on Jun. 4, 2010, now abandoned.

(60) Provisional application No. 61/184,082, filed on Jun. 4, 2009, provisional application No. 61/369,192, filed on Jul. 30, 2010.

(51) Int. Cl.
*G01V 5/00* (2006.01)
*G06F 17/40* (2006.01)
*G01N 23/04* (2006.01)

(52) U.S. Cl.
CPC .............. *G01V 5/0083* (2013.01); *G06F 17/40* (2013.01); *G01N 23/04* (2013.01)
USPC ................. 702/187; 73/865.8; 378/57; 702/1; 702/127; 702/189; 709/201; 709/217

(58) Field of Classification Search
CPC ........... G01D 7/00; G01D 9/00; G01D 21/00; G01N 23/00; G01N 23/02; G01N 23/04; G01N 33/00; G01N 2223/00; G01T 1/00; G01V 5/00; G01V 5/0008; G01V 5/0083; G06F 11/00; G06F 11/30; G06F 11/32; G06F 11/34; G06F 15/00; G06F 15/16; G06F 17/00; G06F 17/40; G06F 17/60; G06F 19/00
USPC ............. 73/52, 432.1, 865.8, 866.3; 250/306, 250/307, 336.1, 358.1; 378/1, 51, 57, 62, 378/63; 702/1, 127, 187, 188, 189; 705/1.1, 705/16, 28, 330, 333, 341; 709/201, 217, 709/218, 219
See application file for complete search history.

(56) References Cited

U.S. PATENT DOCUMENTS

2,883,255 A * 4/1959 Anderson ....................... 346/34
3,428,803 A * 2/1969 Grundhauser et al. ........ 250/306
(Continued)

*Primary Examiner* — Edward Cosimano (57) ABSTRACT

Systems and methods for container analysis and tracking. A method includes scanning a plurality of items by a first data processing system to generate x-ray image data of the items, each of the plurality of items having a unique identifier. The method includes performing a computer implemented image recognition process on the x-ray image data to identify the items. The method includes interactively reviewing the x-ray image data with a human operator by a second data processing system, including displaying the x-ray image data to the human operator. The method includes recording the result of the human operator's review. The method includes determining, for each item, if the results from the computer implemented image recognition process and interactive review meet criteria for items that are exceptions that should not be shipped, and storing an exception indicator for each item using the respective unique identifier.

19 Claims, 6 Drawing Sheets

(56) References Cited

U.S. PATENT DOCUMENTS

| | | | |
|---|---|---|---|
| 3,534,337 A * | 10/1970 | Martin et al. | 702/188 |
| 5,301,122 A * | 4/1994 | Halpern | 702/62 |
| RE35,793 E * | 5/1998 | Halpern | 702/62 |
| 5,930,773 A * | 7/1999 | Crooks et al. | 705/30 |
| 5,943,656 A * | 8/1999 | Crooks et al. | 705/30 |
| 6,035,285 A * | 3/2000 | Schlect et al. | 705/30 |
| 6,052,671 A * | 4/2000 | Crooks et al. | 705/34 |
| 6,088,688 A * | 7/2000 | Crooks et al. | 705/412 |
| 6,843,599 B2 * | 1/2005 | Le et al. | 378/198 |
| 7,322,745 B2 * | 1/2008 | Agrawal et al. | 378/198 |
| 7,324,921 B2 * | 1/2008 | Sugahara et al. | 702/183 |
| 7,369,643 B2 * | 5/2008 | Kotowski et al. | 378/57 |
| 7,517,149 B2 * | 4/2009 | Agrawal et al. | 378/57 |
| 7,519,148 B2 * | 4/2009 | Kotowski et al. | 378/57 |
| 7,783,004 B2 * | 8/2010 | Kotowski et al. | 378/57 |
| 7,817,776 B2 * | 10/2010 | Agrawal et al. | 378/57 |
| 7,876,880 B2 * | 1/2011 | Kotowski et al. | 378/57 |
| 7,957,505 B1 * | 6/2011 | Katz et al. | 378/57 |
| 7,963,695 B2 * | 6/2011 | Kotowski et al. | 378/198 |
| 8,059,781 B2 * | 11/2011 | Agrawal et al. | 378/57 |
| 8,275,091 B2 * | 9/2012 | Morton et al. | 378/57 |
| 8,279,067 B2 * | 10/2012 | Berger et al. | 340/572.1 |
| 8,356,937 B2 * | 1/2013 | Kotowski et al. | 378/198 |
| 8,668,386 B2 * | 3/2014 | Morton et al. | 378/198 |
| 2004/0017887 A1 * | 1/2004 | Le et al. | 378/57 |
| 2005/0157842 A1 * | 7/2005 | Agrawal et al. | 378/27 |
| 2007/0217572 A1 * | 9/2007 | Kotowski et al. | 378/57 |
| 2007/0276619 A1 * | 11/2007 | Sugahara et al. | 702/82 |
| 2008/0075232 A1 * | 3/2008 | Agrawal et al. | 378/198 |
| 2008/0165926 A1 * | 7/2008 | Kotowski et al. | 378/57 |
| 2009/0116614 A1 * | 5/2009 | Kotowski et al. | 378/57 |
| 2009/0245462 A1 * | 10/2009 | Agrawal et al. | 378/57 |
| 2009/0274270 A1 * | 11/2009 | Kotowski et al. | 378/57 |
| 2010/0189226 A1 * | 7/2010 | Kotowski et al. | 378/198 |
| 2011/0038453 A1 * | 2/2011 | Morton et al. | 378/57 |
| 2011/0116597 A1 * | 5/2011 | Agrawal et al. | 378/57 |
| 2012/0121072 A1 * | 5/2012 | Kotowski et al. | 378/198 |
| 2013/0016636 A1 * | 1/2013 | Berger et al. | 370/310 |
| 2013/0230148 A1 * | 9/2013 | Morton et al. | 378/198 |

* cited by examiner

CONTAINER TRANSPORT MONITORING AND ANALYSIS

CROSS-REFERENCE TO OTHER APPLICATION

This application is a continuation-in-part of U.S. patent application Ser. No. 12/802,392, filed Jun. 4, 2010, now abandoned, which claims the benefit of the filing date of expired U.S. Provisional Patent Application 61/184,082, filed Jun. 4, 2009, both of which are hereby incorporated by reference. This application also claims the benefit of U.S. Provisional Patent Application 61/369,192, filed Jul. 30, 2010, which is hereby incorporated by reference.

TECHNICAL FIELD

The present invention relates to systems and methods for the security screening of air and marine cargo.

BACKGROUND OF THE DISCLOSURE

To reduce the threat against passenger airlines that carry cargo, the US Congress has enacted legislation that mandates screening of all air cargo transported on passenger aircraft by August 2010 to a level commensurate with that of passenger baggage. Improved systems and methods are desirable.

SUMMARY OF THE DISCLOSURE

Various disclosed embodiments include systems and methods for container analysis and tracking. In one embodiment, a method includes scanning a plurality of items by a first data processing system to generate x-ray image data of the items, each of the plurality of items having a unique identifier. The method includes performing a computer implemented image recognition process on the x-ray image data to identify the items. The method includes interactively reviewing the x-ray image data with a human operator by a second data processing system, including displaying the x-ray image data to the human operator. The method includes recording the result of the human operator's review. The method includes determining, for each item, if the results from the computer implemented image recognition process and interactive review meet criteria for items that are exceptions that should not be shipped, and storing an exception indicator for each item using the respective unique identifier.

Another embodiment includes a method performed by a plurality of interconnected data processing systems. The method includes photographing a plurality of items in human-visible light by a first data processing system to generate photographic image data of the item, each of the plurality of items having a unique identifier. The method includes scanning the plurality of items by the first data processing system to generate x-ray image data of the items. The method includes interactively reviewing the x-ray image data and photographic image data with a human operator by a second data processing system, including displaying the x-ray image data and photographic image data to the human operator. The method includes recording the result of the human operator's review and determining, for each item, if the results of the interactive review meet criteria for items that are exceptions that should not be shipped. The method includes storing an exception indicator for each item using the respective unique identifier.

Another disclosed method includes checking a container using a decentralized container checking device to produce a data record. The method includes transmitting container checking device. The method includes processing the data record from the check data processing device with regard to a transport procedure of the container, and making the data record available for retrieval by a decentralized organization. A security measure can be initiated according to the data record.

Another embodiment includes a system configured to interact with a decentralized container checking device which is provided for local checking of a container, comprising. The system includes a central data processing system remote from the container checking device. The system includes a first interface configured to provide a data communication between the central data processing system and the decentralized container checking device. The central data processing system processes in at least a first operating mode a data record captured by the decentralized container checking device corresponding to a transport procedure of the container. The system includes at least one second interface configured to make the data record processed by the central data processing system available for calling-up by a decentralized organization. A security measure can be initiated according to the data record.

Another embodiment includes a system including at least one container checking device having has a checking unit for local checking of a container. The system includes a check data processing device configured for use with the container checking device. The container checking device has an interface unit configured to communicate with a first interface of the check data processing device.

The foregoing has outlined rather broadly the features and technical advantages of the present disclosure so that those skilled in the art may better understand the detailed description that follows. Additional features and advantages of the disclosure will be described hereinafter that form the subject of the claims. Those skilled in the art will appreciate that they may readily use the conception and the specific embodiment disclosed as a basis for modifying or designing other structures for carrying out the same purposes of the present disclosure. Those skilled in the art will also realize that such equivalent constructions do not depart from the spirit and scope of the disclosure in its broadest form.

Before undertaking the DETAILED DESCRIPTION below, it may be advantageous to set forth definitions of certain words or phrases used throughout this patent document: the terms "include" and "comprise," as well as derivatives thereof, mean inclusion without limitation; the term "or" is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, whether such a device is implemented in hardware, firmware, software or some combination of at least two of the same. It should be noted that the functionality associated with any particular controller may be centralized or distributed, whether locally or remotely. Definitions for certain words and phrases are provided throughout this patent document, and those of ordinary skill in the art will understand that such definitions apply in many, if not most, instances to prior as well as future uses of such defined words and phrases. While some terms may include a wide variety of embodiments, the appended claims may expressly limit these terms to specific embodiments.

BRIEF DESCRIPTION OF THE DRAWINGS

For a more complete understanding of the present disclosure, and the advantages thereof, reference is now made to the following descriptions taken in conjunction with the accompanying drawings, wherein like numbers designate like objects, and in which.

DETAILED DESCRIPTION

FIGS. 1 through 6 discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged device. The numerous innovative teachings of the present application will be described with reference to exemplary non-limiting embodiments.

Disclosed embodiments include systems and methods for improved cargo screening. There are various means of screening that provide a level commensurate with passenger bags, including physical search, x-ray scanning, computed tomography (CT) scanning, and explosive trace detector (ETD) equipment. In some cases, multiple means are employed sequentially, such as the case in which the x-ray results are unclear, and an item may be either physically searched or processed in ETD equipment as a second step.

Cargo carried in wide-body passenger aircraft is typically loaded in Unit Load Devices (ULDs), secure containers of standard size which can be prepared of site by shippers or freight forwarding services. As used herein, ULD, "transport unit", and containers are all used to refer to shipping containers, regardless of the specific type or configuration, and may be used interchangeably.

Disclosed embodiments also include data processing systems for use with a decentralized container checking device that can perform local checking of a container.

The transport of goods is growing steadily given the current development of the global economy. Transport over long-haul, in particular intercontinental routes is particularly affected by this increase. With this trend the importance of the checking of transport containers in relation to the security-related aspects of these transport processes is likewise growing. It becomes increasingly important, particularly for official authorities in a destination country, to provide for a rapid and flexible checking of transport containers that are provided for import into the destination country.

Figure 1:
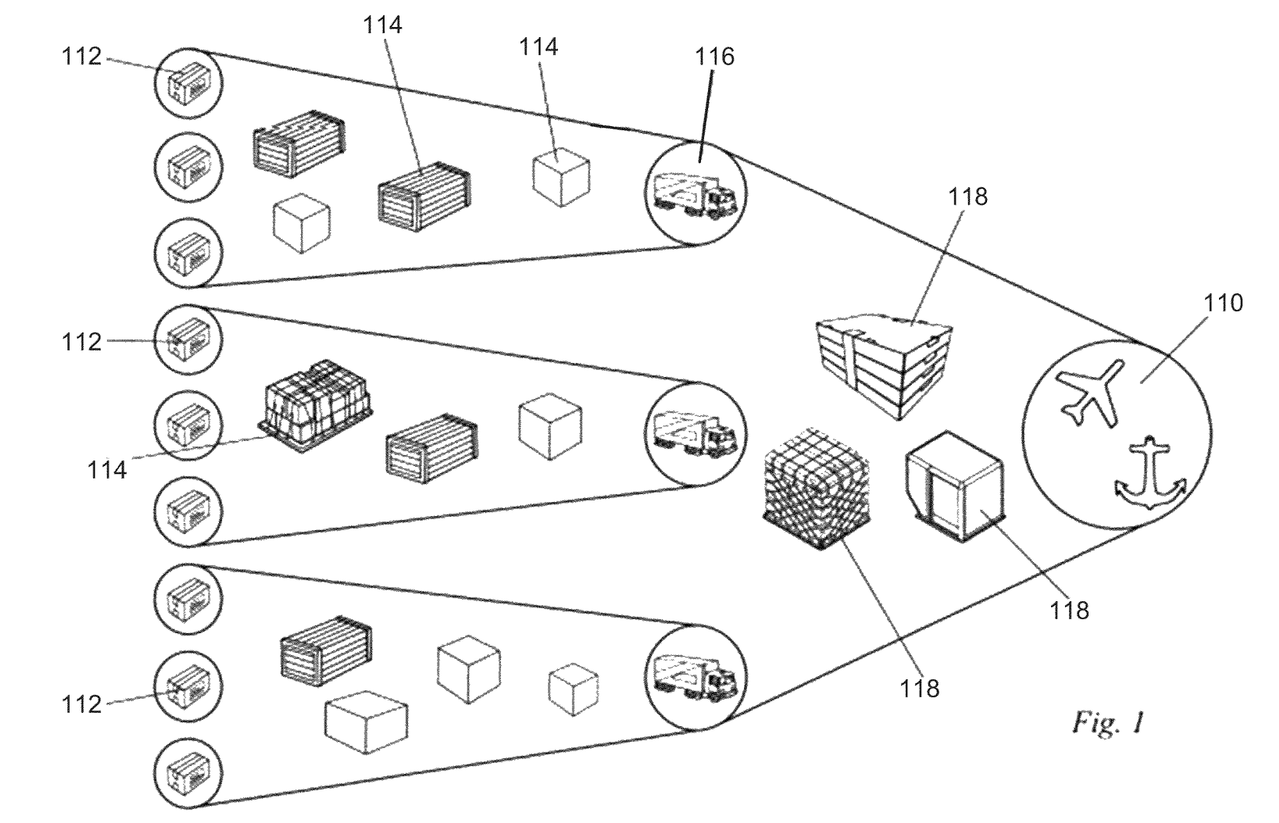
FIG. 1 shows the processing flow of cargo to airports or seaports as described herein.

FIG. 1 shows the processing flow of cargo to airports or seaports 110. Individual shippers 112 prepare and ship their packaged goods 114 or other cargo items to be delivered to customers and other recipients. These packaged goods 114 can be transported by freight forwarders 116. The packaged goods 114, before being transported on an aircraft or ship, can be loaded into ULDs or other containers 118 (generically referred to as containers 118). This can be performed off site by shippers 112 or freight forwarders 116, or by other parties. The ULDs or other containers 118 are delivered to the airports or seaports 110, and transported from there to another airport or seaport.

One goal of inspection procedures is to scan or otherwise inspect each container 118 before loading it into a transport vehicle such as a plane or ship, preferably without having to open a container 118 or any packaged item 114 inside it. In FIG. 1, packaged goods 114 are aggregated into relevant containers 118 in processing.

Current scanning systems require that the items loaded in a container 118 to be unloaded and screened individually and serially. Some shippers or freight forwarders attempt to comply with the new U.S. legislation by deploying x-ray scanning equipment to points in the preparation chain prior to the loading of containers 118, and use specially trained operators to screen cargo destined for containers 118 ahead of time. The chain of custody from the point of screening to the aircraft must be carefully observed, and records are transmitted to the Transportation and Security Administration (TSA) after the fact. X-ray scanning products must be certified by the TSA for security screening applications.

Scanning systems themselves include three principal functions, which are tightly integrated in a proprietary package. The systems include x-ray scanning to create an electronic image of the item and its contents. The systems use varying degrees of automatic recognition of the electronic images. The systems use a human-machine interface (HMI) for screening, where a certified operator is shown the image with pre-knowledge from the automatic recognition, and the operator is provided controls to capture operator input, including comments, regarding each image.

For example, if an item in the image can be reliably recognized by software analysis of the image, then it is classified as ordinary or potentially dangerous. Image recognition analysis may for example reveal that an item shown is being shielded by another item and that that the image review results will not be reliable, requiring a manual inspection.

Figure 2:
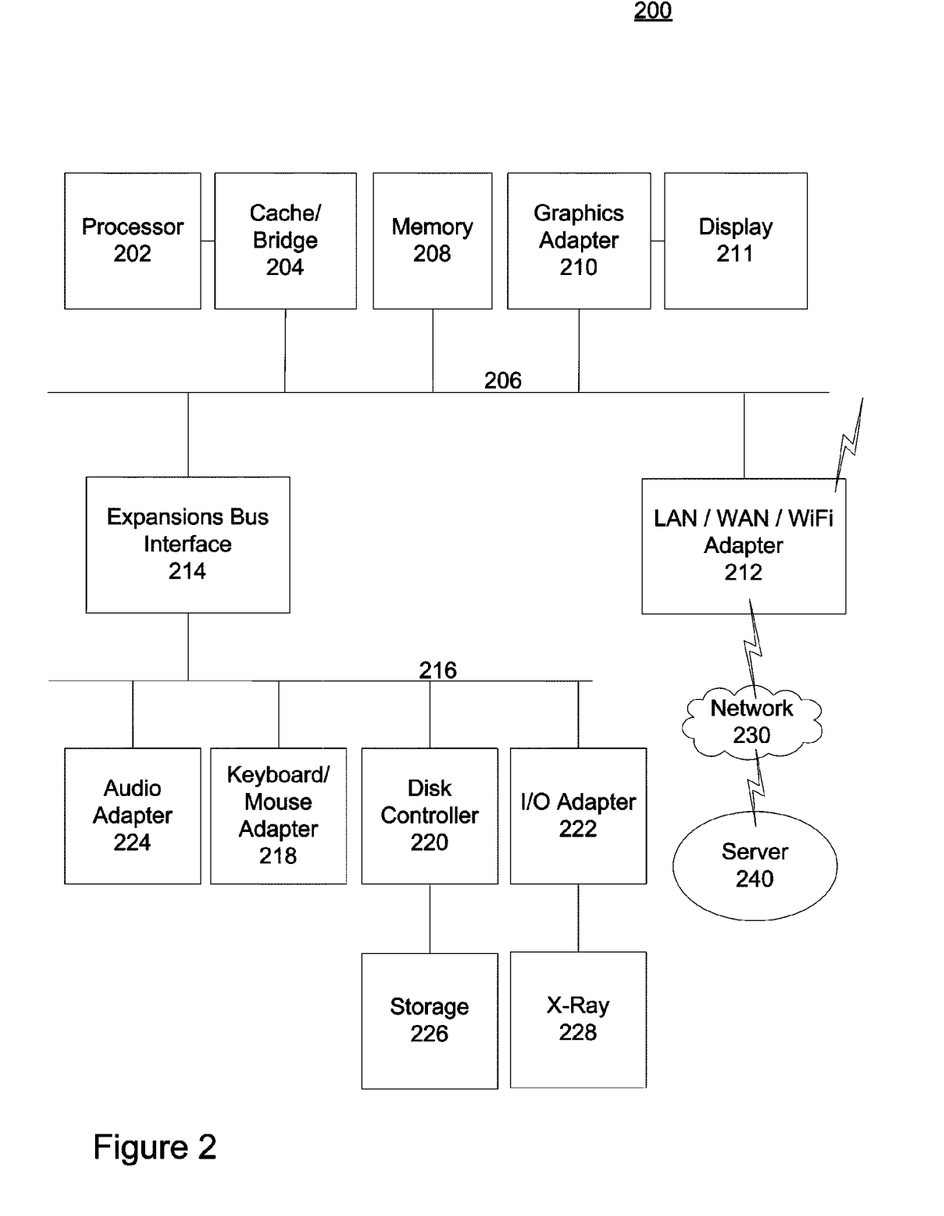
FIG. 2 depicts a block diagram of a data processing system in which an embodiment can be implemented.

FIG. 2 depicts a block diagram of a data processing system 200 in which an embodiment can be implemented, for example as one of the systems or servers described below, and can be configured to perform processes as described herein. The data processing system 200 depicted includes a processor 202 connected to a level two cache/bridge 204, which is connected in turn to a local system bus 206. Local system bus 206 may be, for example, a peripheral component interconnect (PCI) architecture bus. Also connected to local system bus in the depicted example are a main memory 208 and a graphics adapter 210. The graphics adapter 210 may be connected to display.

Other peripherals, such as local area network (LAN)/Wide Area Network/Wireless (e.g. WiFi) adapter 212, may also be connected to local system bus 206. Expansion bus interface 214 connects local system bus 206 to input/output (I/O) bus 216. I/O bus 216 is connected to keyboard/mouse adapter 218, disk controller 220, and I/O adapter 222. Disk controller 220 can be connected to a storage 226, which can be any suitable machine usable or machine readable storage medium, including but not limited to nonvolatile, hard-coded type mediums such as read only memories (ROMs) or erasable, electrically programmable read only memories (EEPROMs), magnetic tape storage, and user-recordable type mediums such as floppy disks, hard disk drives and compact disk read only memories (CD-ROMs) or digital versatile disks (DVDs), and other known optical, electrical, or magnetic storage devices.

I/O adapter 222 can also be connected directly or indirectly, in some embodiments, to an X-ray scanner/imager 228 for performing the scanning and imaging functions described below, and can be connected to communicate images and other information with the remainder of data processing system 200 via I/O adapter 222. X-ray scanner/imager 228 can be implemented as a stand-alone device or integrated with data processing system 200, and the images and other information can be communicated to other systems, servers, and networks as described herein. In other cases, as described herein, the I/O adapter 222 can be connected to other input devices, such as barcode or RFID readers.

Also connected to I/O bus 216 in the example shown is audio adapter 224, to which speakers (not shown) may be connected for playing sounds. Keyboard/mouse adapter 218 provides a connection for a pointing device (not shown), such as a mouse, trackball, trackpointer, etc.

Those of ordinary skill in the art will appreciate that the hardware depicted in FIG. 2 may vary for particular implementations. For example, other peripheral devices, such as an optical disk drive and the like, also may be used in addition or in place of the hardware depicted. The depicted example is provided for the purpose of explanation only and is not meant to imply architectural limitations with respect to the present disclosure.

A data processing system in accordance with an embodiment of the present disclosure includes an operating system employing a graphical user interface. The operating system permits multiple display windows to be presented in the graphical user interface simultaneously, with each display window providing an interface to a different application or to a different instance of the same application. A cursor in the graphical user interface may be manipulated by a user through the pointing device. The position of the cursor may be changed and/or an event, such as clicking a mouse button, generated to actuate a desired response.

One of various commercial operating systems, such as a version of MICROSOFT WINDOWS™, a product of Microsoft Corporation located in Redmond, Wash. may be employed if suitably modified. The operating system is modified or created in accordance with the present disclosure as described.

LAN/WAN/Wireless adapter 212 can be connected to a network 230 (not a part of data processing system 200), which can be any public or private data processing system network or combination of networks, as known to those of skill in the art, including the Internet. LAN/WAN/Wireless adapter 212 can also communicate with other elements of the systems described herein, and each data processing system 200 can perform other data processing system or server processes described herein. Data processing system 200 can communicate over network 230 with one or more server systems 240, which are also not part of data processing system 200, but can be implemented, for example, as separate data processing systems 200.

Various embodiments can use a data processing system 200 with a decentralized container checking device for the local checking of a container. In various embodiments, such a system can include a central data processing system remote from the container checking device, a first interface which creates a data communication between the central data processing system and the decentralized container checking device, where the central data processing system processes a data record captured by the decentralized container checking device in at least one operating mode in respect of a transport procedure of the container, and at least one second interface, which makes the data record processed by the central data processing system available for calling-up by a decentralized organization, which serves to initiate a security measure depending on the data record. With the aid of a first interface, a data record captured by the decentralized container checking device can be quickly accessed by or transmitted to the central data processing system. By means of the second interface, the data record processed by the data processing system can be called up by the organization in a particularly flexible manner, independently of the location of the decentralized container checking and the central data processing system. According to various embodiments, data relating to a check performed on the container prior to the arrival can be collected before the arrival of the container at a destination or prior to on-site checking by the organization. The organization can thereby initiate a security measure relating to this container before the actual arrival of the container, if, for example, it becomes aware of suspicious events in connection with the transport of the container or of an inadequate investigation of the transport at the starting location and/or an intermediate station unit. With the detection of problems in connection with a container, a security level can be assigned to the container, for which predefined security measures are to be initiated. With the aid of the central check data processing device the organization can accordingly perform a classification of containers according to their respectively assigned security level.

In some embodiments, the first interface can communicate with a plurality of decentralized container checking devices at different locations remote from each other. The second interface can additionally be provided in order to make the data record available for calling-up by a multiplicity of different organizations which are remote from each other. The central data processing system is in particular suitable for use as a server which can be made use of by different interested parties on a decentralized basis. These parties can include an official authority, for example a customs authority, an internal security authority, a border control body, a coastguard, etc., which has at its disposal suitable means for performing a security measure. One or more of the systems and devices described herein can have a user interface that can be operated on a decentralized basis by personnel of the organization for calling up data records from the central data processing system.

As used herein, the term "data processing" should be taken to mean in particular the forwarding, processing, conversion, encryption, storage, archiving, assignment, collation, provision, analysis, etc. of data. The term "checking" in connection with a container should in particular be taken to mean the monitoring and/or the investigation of the container. Checking can for example mean an investigation of the contents, monitoring of the container and/or its environment, an inspection of the state of a seal, etc. The term "container" should in particular be understood as a transport unit, ULD, or other unit specially equipped for the transport of goods. Disclosed embodiments are particularly suitable for the checking of transport containers, for example of standardized transport containers, which are specially designed for road, air, rail and/or maritime transport. The container can further be embodied as a pallet or package. The term "provided" should in particular be taken to mean specially designed, equipped, embodied and/or programmed.

A decentralized container checking device is provided for "local" checking, in that it preferably has at least one checking device, which is arranged in the vicinity, preferably in the immediate vicinity, of the container, such as for example an optical monitoring system, a screening device, etc. The terms "central" and "decentralized", with respect to units forming a system, refer to a system for which the arrangement of a decentralized unit relative to the central unit for the operation of the entire system in respect of a task to be performed is of no significance. To this end a data communication between the central unit and a decentralized unit preferably takes place via, at least one data network, to which at least nationwide, preferably worldwide access is possible. The data communication preferably takes place by means of a terrestrial network and/or a satellite network. In particular a remote checking of the container can takes place by means of the central data processing system, where remoteness of the decentralized container checking device from the central data processing system is of no significance for performing checking function, or the performing of the checking function is not dependent on the remoteness.

In some embodiments, the transfer of the data record, the processing of the data record, and the provision of the same are embodied as very largely real-time processes. The organization can hereby be immediately supplied with data, which corresponds to the current checking status of the container, where particularly early security measures can be initiated by the organization upon the incidence of a suspicious event. Alternatively or additionally, data acquired by the decentralized container checking device is stored or archived by the central data processing system for a later calling-up by the organization or a further organization.

Such checking processes are particularly effective if the central data processing system is provided to analyze the data record for determining a security-related event affecting the transport procedure. The central data processing system can be programmed to recognize a predefined event, on the basis of at least one data record of the decentralized container checking device. This can for example be by means of a comparison of the at least one data record with stored data, such as in particular entries in a database. The occurrence of a known suspicious event, in relation to security, such as for example the breaking-open of a sealed container or an inadequately or improperly performed investigation of the container, can thereby be automatically and rapidly detected, and a security measure can accordingly be initiated.

An inadequate investigation of the container can be detected at an early stage. In various embodiments, the first interface is provided to create a data communication between the central data processing system and the decentralized container checking device, which is operated in connection with an investigation of the container for the presence of non-permitted contents. The investigation can take place in a security area protected according to security provisions preparatory to the transport procedures, and the central data processing system is provided in at least one operating mode to process the data record in respect of a security-related event occurring during the investigation. The security area can have a security zone which is separated from its environment and for which certain physical access conditions are provided.

In some embodiments, the central data processing system can process the data record in respect of an event affecting the security area, so that the observance of security provisions can be checked by the organization for in connection with the investigation of the container within the security area. For example, the entry and exit of persons into/out of the security area can be monitored by means of the check data processing device, via which data relating to the security area is transmitted to the organization. The registering of further events which occur during the presence of the container in the security area, such as for example damage to the container, failure of the video monitoring, etc. is likewise possible.

Information relating to possibly suspicious contents of the container and/or an investigation which is inadequately performed, for example incompletely performed, can be transmitted rapidly and flexibly to the organization, particularly in cases where the central data processing system processes the data record in respect of the contents of the container.

Problems in connection with an investigation of the container in the security area can additionally be detected early in embodiments where the central data processing system is provided in at least one operating mode in interoperation with the decentralized container checking device, in order to make the data record available for review up during the presence of the container in the security area.

Security at the destination can likewise be enhanced in that the first interface is provided to communicate between the central data processing system and the decentralized container checking device, which is embodied as a mobile device accompanying the container during a transit of the same. The incidence of a security loophole in the period between a contents inspection at a starting location or at an intermediate station and the arrival at the destination can thereby advantageously be prevented.

In some embodiments, early security measures can be initiated by the organization upon the incidence on suspicious events during the transit of the container, in cases where the central data processing system in at least one operating mode in interoperation with the decentralized container checking device is provided, to make the data record available to the decentralized organization during transit of the container. A preferably permanent or at least regular monitoring of the container in a transport means for transit of the same can thereby be effected by the organization.

Figure 3:
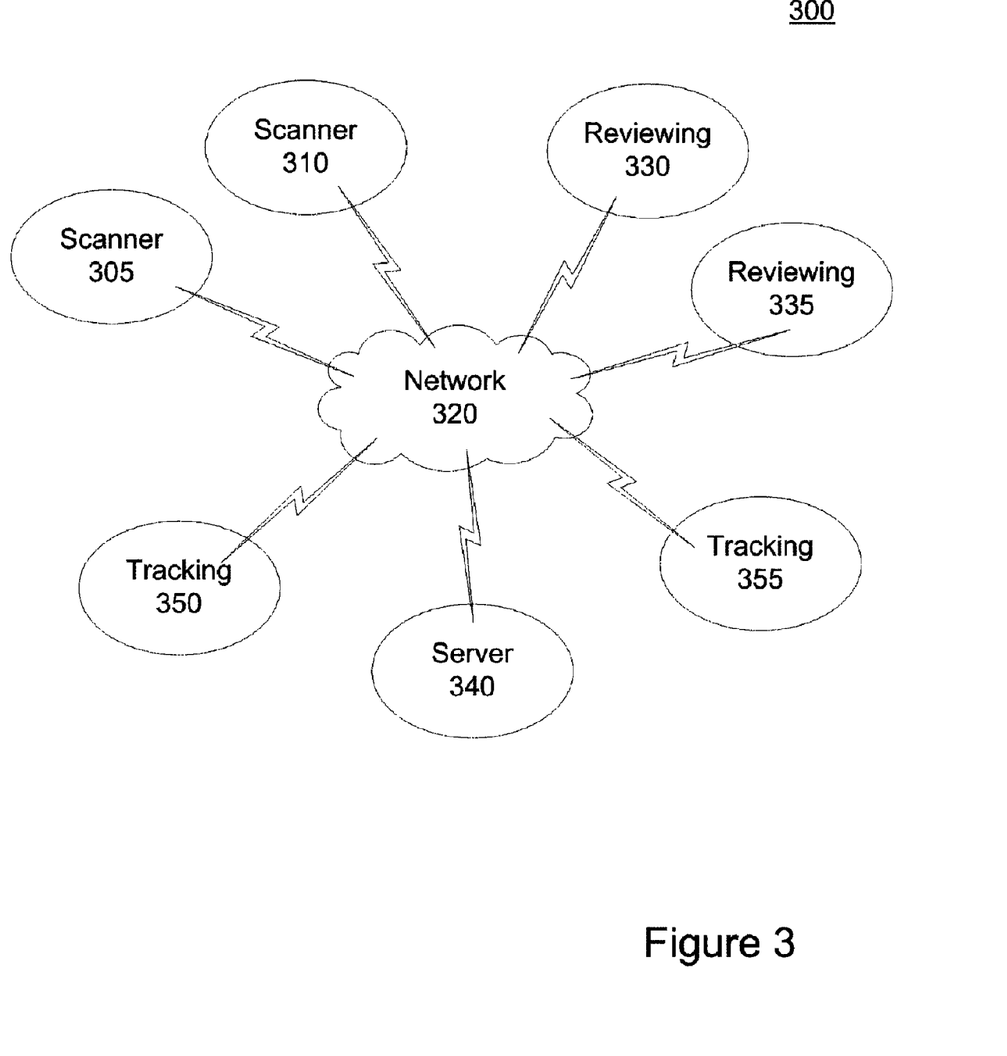
FIG. 3 shows a simplified block diagram of a distributed screening and tracking system as described herein.

FIG. 3 shows a simplified block diagram of a distributed screening and tracking system 300 as described herein. In this figure, scanners 305 and 310 act as the decentralized container checking devices, each can include a scanning imager, such as an x-ray scanner/imager or otherwise, that is capable of producing, storing, and transmitting a scanned image of the contents of a container. Each of scanners 305 and 310 can be implemented, for example, as a data processing system 200. While two scanners are shown in this example, those of skill in the art will recognize that any number of scanners can be connected and configured to perform as described herein.

Scanners 305 and 310 are connected to communicate over network 320, which can be any combination of public and private networks.

Reviewing stations 330 and 335 can be implemented as data processing systems 200, and are configured to perform processes as described herein. Reviewing stations 330 and 335 are configured to receive, store, and display scanned images received from one or more scanners over the network 320. Reviewing stations 330 and 335 are configured to interactively review the scanned images with a user, to receive and store any user input related to the images as part of the container data described below, and to indicate which containers include exceptions that must be removed and manually screened.

The system can also include one or more central servers 340, implementing the central data processing systems described herein, which can receive and maintain the container data described herein, and communicate it to any of the other described systems as required, and can be implemented as a data processing system 200.

The system can also include one or more tracking stations 350 and 355, which can access and display container data for any container, and can be implemented as data processing systems 200. The tracking stations can be used to review container data for any container before it is loaded onto any transport, so that any exceptions can be removed or otherwise handled, to track the status of the container during loading, unloading, or transit, or to perform other functions as described herein. The tracking stations need not include either x-ray scanners or sufficient capacity to perform the automated image recognition described herein.

The automatic image analysis functions described herein can be performed by the reviewing stations, by the scanners, or both, depending on implementation.

Figure 4:
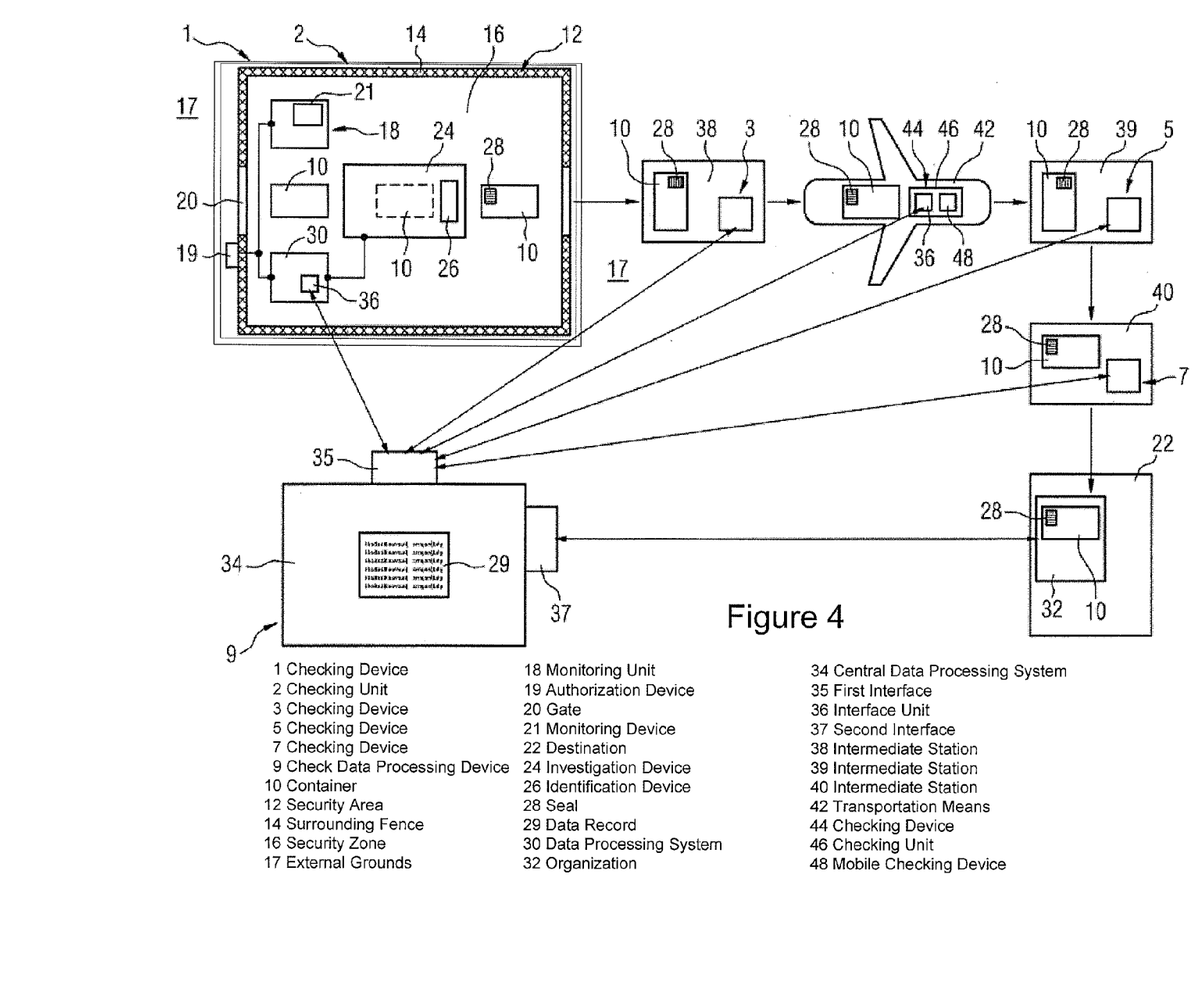
FIG. 4 shows a schematic representation of another exemplary system in accordance with disclosed embodiments.

FIG. 4 shows a schematic representation of another exemplary system in accordance with disclosed embodiments, comprising decentralized container checking devices and a central check data processing device 9. FIG. 4 shows, in a schematic view, a system comprising a set of container checking devices 1, 3, 5, 7, 44 and a check data processing device 9.

The container checking device 1 has a checking unit 2, which is provided for local, on-site checking of a container 10. The checking unit 2 has a security area 12 shown from above, in which containers 10 are subject to investigation of their contents within the framework of the handling of a transport procedure. In the present example, the container 10 represented is embodied as a freight container, in particular as a standardized cargo container. The security area 12 has a surrounding fence 14, which serves to delimit a security zone 16 and to prevent unauthorized access to this security zone 16. Access to the security zone 16 or presence in the security zone 16 are subject to security provisions, which relate in particular to the authorization of personnel and the equipping of the security area 12 with control and monitoring means, whereby the security zone 16 is protected in relation to external grounds 17 or has a higher security level than the external grounds 17.

The security area 12 is monitored by means of a monitoring unit 18, which serves to register security-related events in connection with the security area 12. To this end, the monitoring unit 18 has an access authorization device 19, which regulates access to the security zone 16. This controls a gate 20, where only authorized persons may be present in the security zone 16. The access authorization device 19 can for example have a reader unit, which permits access by means of an ID badge. Alternatively or additionally the access authorization device 19 has a recording unit, which serves to capture biometric characteristics, such as for example a fingerprint. The monitoring unit 18 further has a monitoring device 21 for the permanent monitoring of the security zone 16. This can for example have a video camera, an infrared sensor, a movement detector, etc.

Preparatory to a transport procedure, in which a container 10 is to be transported from a starting location to a destination 22, an unchecked container 10 is transferred into the security area 12. To perform the investigation the checking unit 2 has an investigation device 24 in the security zone 16, by means of which the contents of the container 10 is checked in respect of illegal materials, such as for example illegal drugs, explosives, etc. and/or for characteristics which could potentially endanger safety/security during the transport and at the destination. The investigation device 24 can be provided for the manual scanning of the contents by personnel and/or by a trained animal and/or it can have means for scanning the contents by means of an investigation signal, such as for example an X-ray beam.

If the container 10 is approved for the transport procedure, this is uniquely marked by means of an identification device 26 as an approved container 10, where this identification represents a mandatory prerequisite for transport approval. The marking of the container 10 by means of identification device 26 can take place in different ways, whereby the marking can take place manually, semi-automatically or fully-automatically. For example the container 10 can be marked by means of seal 28, which is for example embodied as a lead seal. In an alternative embodiment, the marking can be through the application of a barcode to the container 10 and/or through the programming of a chip affixed to the container 10, such as for example an RFID. After the marking of the container 10 this is transported from the security area 12 for initiation of the transport procedure or it can be made available in the security zone 16 and transported away from there at a later point in time.

The container 10 is represented in the security zone 16 prior to its investigation as unchecked container 10, during investigation in the investigation device 24 and as an approved container 10 with the identifier, specifically the seal 28. During the presence of the container 10 in the security area 12 a data record 29 is created, which is uniquely assigned to the container 10. The data record 29 contains data relating to the investigated contents of the container 10. Further, data is collected during the presence of the container 10, which relates to the security area 12. For example data can be incorporated into the data record 29 which relates to employees' access to the security zone 16. For example any access authorizations which have taken place before the container 10 has left the security area 12 can be registered. In addition the data from the monitoring device 21 can be added to the data record 29. Events occurring in the security area 12 during the presence of the container 10 can thus be registered in the data record 29. To this end a data processing system 30 is assigned to the security area 12, which captures data from the access authorization device 19, the monitoring device 21, and the investigation device 24, and creates the corresponding data record 29.

The data record 29 is made available to the organization 32 affected by the transport procedure at the destination location 22. A customs authority or border protection agency assigned to the destination 22 can, for example, interrogate the data record 29 and evaluate it in respect of potentially suspicious events in relation to the investigation of the container 10 in the security area 12. This takes place by means of the check data processing device 9, which is used in interoperation with the container checking device 1.

The check data processing device 9 has a central data processing system 34, which serves to process the data record 29 captured by the container checking device 1 in respect of the transport procedure of the container 10. Data interfaces provided for the creation of a data communication between the central data processing system 34 and the container checking device 1, where the check data processing device 9 has a first interface 35, which serves to create the data communication with an interface unit 36 of the container checking device 1, and in particular its data processing system 30. This is in interoperation with the access authorization device 19, with the monitoring device 21 and with the investigation device 24, so that data from these devices can be sent to the check data processing device 9 via the interface unit 36.

The data transfer between the first interface 35 and the interface unit 36 takes place via a data network which is not represented in greater detail, which corresponds to a terrestrial and/or a satellite network. Any desired relative arrangement of the container checking device 1 and the check data processing device 9 can exist, as the data network enables remote access by the central data processing system 34 to a data record 29 of the decentralized container checking device. For example, these devices can be arranged in different continents.

The check data processing device 9 further has a second interface 37, which serves the creation of a data communication with the organization 32. Via this interface 37, the data record 29 processed by the central data processing system 34 is made available for calling-up by the organization 32. In a first embodiment variant the data communication for transfer of the data record 29 between the decentralized container checking device 1 and the central data processing system 34 and between this and the organization 32, the processing of the data record 29 and the provision of the same by the central data processing system 34 are very largely embodied as real time processes. Accordingly, the organization 32 can check the course of the investigation processes in the security area 12 in real-time and preferably permanently.

Alternatively or additionally, in another embodiment, the central data processing system 34 can collect data from the decentralized container checking device 1, which remains available to the organization 32 for calling up at any desired point in time. During the presence of the container 10 in the security area 12 and after its departure from the security area 12, for example during a transit of the container 10 in a transport means, the data record 29 remains available to the organization for calling up. It is also possible for the data record 29 to continue to remain available after the container 10 has reached the destination 22.

The central data processing system 34 can have different operating modes, which relate to the nature of the data received by the decentralized container checking device 1. In one operating mode the data processing system 34 can process the data record 29 in respect of the monitoring of the security area 12. Thus suspicious events can be determined, which have occurred in connection with the security area 12, such as for example the intrusion of an unauthorized person into the security zone 16, the presence of a person in the immediate environs of the container 10, damage to the container 10, etc. In a further operating mode the central data processing system 34 processes the data record 29 in respect of the contents of the container 10. For example it can process an investigation report of the investigation device 24. An inadequate investigation of the contents of the container 10 can hereby be determined, such as for example an incomplete investigation or the failure to observe security provisions during the investigation.

The processing of the data record 29 can depend on the characteristics of the capture of data by the container checking device it, that is, on the manner in which this data is made available, and/or on the wishes of the organization 32 as commissioning party vis-à-vis the operator of the check data processing device 9 as the service provider. The data record 29 can thus be made available by the central data processing system 34 without processing, purely for forwarding to the organization 32, which performs an analysis autonomously, or the central data processing system can be provided to analyze the data record 29 for the recording of a security-related event affecting the transport procedure, where an analysis result is provided for calling-up by the organization 32. For example predefined events can be determined by means of the data processing system 34, in that an analysis of the data record 29 is performed with respect to an existing database of events, which is known to the data processing system 34.

During the transport procedure between the location of the investigation in the security area 12 and the task assigned to the organization 32, the container 10 can be temporarily stored at various intermediate stations 38, 39, 40, where the number of intermediate stations is arbitrary. During the presence of the container 10 at an intermediate station, the transit of the container 10 is interrupted. An intermediate station can in particular correspond to a device, in which the mode of transport of the container 10 is switched. For example the intermediate station can be a transshipment railroad station, the cargo area of an airport or a harbor. The intermediate stations 38, 39, 40 are in each case equipped with a container checking device 3, 5 or 7, by means of which the container 10 is checked during the storage period, in particular is monitored. Data which is collected during this monitoring, is added to the data record 29 assigned to the container 10 in the central data processing system 34, so that it is likewise accessible to the organization 32. In particular the identifier, and specifically in the present example the seal 28, is checked by the respective container checking device 3, 5 or 7. If the seal 28 is damaged, this can be ascertained by the organization 32, and special measures provided, before the container 10 is handed over to the organization 32. The container checking devices 3, 5, 7 in each case have an interface unit 36, by means of which a data communication can be created with the first interface 35 of the check data processing device 9.

During its transit in a transport means 42 the container 10 can further be monitored by means of a mobile container checking device 44. This can, as described above, register events affecting the container 10, and in particular can check the state of the seal 28, and the captured data can be added to the data record 29 in the central data processing system 34 via an interface unit 36. To this end the first interface 35 is provided for data communication with the decentralized container checking device 42, which is embodied as a mobile device accompanying the container 10 during its transit. The container checking device 44 has a checking unit 46 for local checking of the container 10 in the transport means 42, which comprises a mobile checking device 48, which accompanies the container 10 during its transit, embodied as video monitoring or monitoring of the seal status. During the transit of the container 10, a data record is captures by the mobile checking device 48 and transmitted by means of the interface unit 36, which interoperates with the mobile checking device 48, to the central data processing system 34 via the first interface 35. The organization 32 can thus track the checking of the container 10 at any time during the transit of the same, or data can be collected during the transit by the central data processing system 34, which can be called up by the organization at a later point in time, for example upon the arrival of the container 10 at the destination 22.

Various disclosed embodiments include methods for screening and tracking items of cargo to be shipped aboard a vehicle, and throughout the shipping process.

Figure 5:
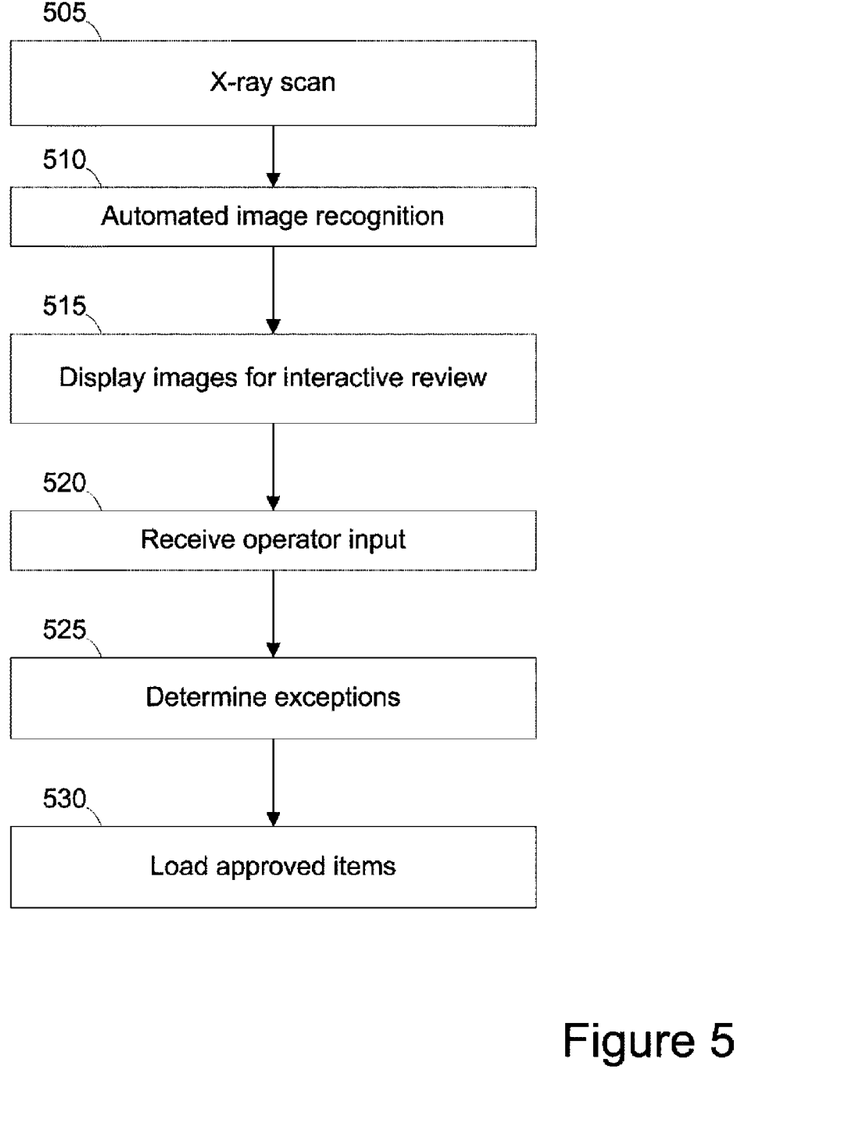
FIGS. 5 and 6 depict flowcharts of processes in accordance with disclosed embodiments.

FIG. 5 depicts a flowchart of such a process in accordance with disclosed embodiments that can be performed by a system as described herein. Note that in some embodiments, the storing, receiving, and loading of data described herein can include sending the data to a server 340 or receiving the data from the server 340.

The system scans items of cargo to generate x-ray image data of items of cargo to be shipped in a container (step 505). This step can be performed, for example, by a scanner 305 operated by a first user. The scan and x-ray image data can include an x-ray scan of the container loaded with multiple cargo items, x-ray scans of at least one of each type of cargo item, and/or x-ray scans of each individual cargo item. This step can include storing the x-ray image data using a unique identifier that is associated with the container and/or the specific item.

The system performs a computer-implemented image recognition process on the x-ray image data to identify the items as automated item identification (step 510). This step can be performed, for example, either by a scanner 305, by a reviewing station 330, or by a server 340. This step can include storing the automated item identification using the unique identifier, and associated with the x-ray image data. In some cases, in this step, the system compares the x-ray image data image to one or more stored images that can include acceptable cargo or exceptions.

The system displays x-ray image data to a human operator trained in object recognition or other user to interactively review the image with the user (step 515). This step can be performed, for example, by a reviewing station 330. As part of this step, the system can also display the automated item identification to the user in some cases, the system can display the stored image or images to the user for comparison with the x-ray image data.

The system receives and stores the result of the user's review as operator item identification (step 520). This step can be performed, for example, by a reviewing station 330, and can include storing the operator item identification using the unique identifier, and associated with the x-ray image data. The human operator can be one of a number of such operators at one or more locations who have access to or receive image data for items to be shipped for each item.

The system determines if the automated item identification and/or the operator item identification for each item meet criteria for "exceptions", which are items that should not be shipped for any of a variety of reasons (step 525). This step can include storing an exception indicator using the unique identifier, and associated with the x-ray image data.

This process can also include loading the cargo items into a shipping container or aboard a vehicle according to the exception identifier (step 530). The items which are not exceptions, the "approved" items, can be loaded into a common container which is then loaded on the vehicle. Exceptions can be handled separately as may be required by the type of item being shipped.

In some cases, a number of items are scanned together, in a container, to generate the image data. In some cases, the operator review steps may not be necessary depending on the certainty of the automated recognition process. Of course, if no decision can be made by automatic image recognition analysis, the image can be presented by HMI or other manual review of the image.

Some embodiments include a distributed review, using a distributed system for the security screening of air cargo that minimizes costs associated with the process. Distributed for purposes of this disclosure means that tasks are performed in a manner that spreads the steps of the process out among different persons, machines and/or locations, including as described above. In particular, the reviewing stations may be geographically remote from the scanners, and the x-ray image data can be transmitted from any number of scanners to any number of reviewing stations, so that the operator review can be performed wherever it is most efficient or there are operators with available capacity for review.

A distributed screening process as described herein can be implemented in various ways according to disclosed embodiments. For example, the scanning/imaging can be performed at an early part of the process, so that any human review of the images can take place while the cargo, container, or ULD is in transit to the airport/seaport or other distribution center, and any processing of exceptions can be handled when the container arrives in other embodiments, the screening can be performed in as few sites as possible, such as at the airports themselves. In this approach, cargo is aggregated at the airport, and is screened prior to loading aboard an aircraft.

As noted herein, typical screening technology does not allow ULDs or other containers to be scanned all at once. In conventional screening processes, the containers must be broken down and screened, then rebuilt and loaded onto the aircraft. While this approach is theoretically viable, it is problematic from the perspective of the freight forwarder, since they can no longer provide prepared cargo, and it represents a labor intensive system bottleneck at the airport. According to the disclosed embodiments, the containers need not be and are not broken open as a normal step of screening. Instead, x-ray scanning can be performed as items are loaded, and the container then sealed, and loaded containers can also be scanned to screen the items in aggregate.

Figure 6:
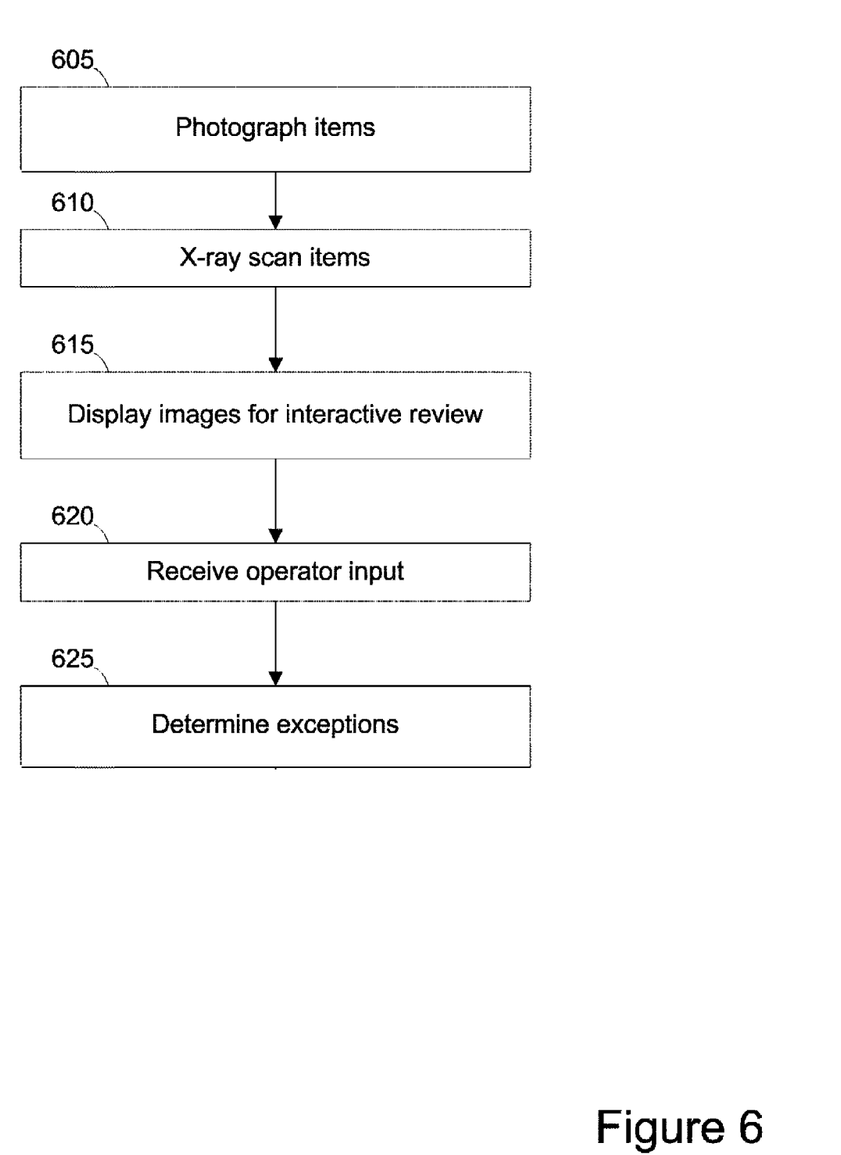

FIG. 6 depicts a flowchart of a process in accordance with disclosed embodiments for screening and tracking items of cargo to be shipped aboard a vehicle.

The system photographs each of a plurality of items in human-visible light to generate photographic image data of the item (step 605). This step can be performed, for example, by a scanner 305 operated by a first user. This step can include storing the photographic image data using a unique identifier that is associated with the item and/or the container into which the items are to be loaded.

The system scans items of cargo to generate x-ray image data of items of cargo to be shipped in a container (step 610). This step can be performed, for example, by a scanner 305 operated by a first user. The scan and x-ray image data can include an x-ray scan of the container loaded with multiple cargo items, x-ray scans of at least one of each type of cargo item, and/or x-ray scans of each individual cargo item. This step can include storing the x-ray image data using the unique identifier that is associated with the container.

The system displays the photographic image data and the x-ray image data of each item a human operator trained in object recognition or other user to interactively review the images with the user (step 615). This step can be performed, for example, by a reviewing station 330. This step can include comparing the photographic image data with the corresponding x-ray image data for each item, and can include displaying one or more stored photographic or x-ray images that can include acceptable cargo, exceptions, or types of items likely to be found in the shipment, for comparison by the user.

The system receives and stores the result of the user's review as operator item identification (step 620). This step can be performed, for example, by a reviewing station 330, and can include storing the operator item identification using the unique identifier, and associated with the x-ray image data. The human operator can be one of a number of such operators at one or more locations who have access to or receive image data for items to be shipped for each item.

The system determines if the operator item identification meet criteria for exceptions (step 625). This step can include storing an exception indicator using the unique identifier, and associated with the x-ray image data and/or the photographic image data.

As above, the operator item identification and exception indicator can be used to determine which items can be loaded or which are exceptions.

Various embodiments improve productivity by breaking up bundled x-ray scanning processes such that different functions do not need to occur at the same place or time. Scanning/imaging and automatic recognition, which do not, in and of themselves, require extensive human training, are therefore distributed. That is, the various functions described herein performed can be performed at a variety of times and locations and are preferably allowed to be widely distributed, that is, taking place at a number of different places. The HMI process can be centralized so that images from the distributed scanning and imaging points are electronically forwarded or otherwise made available to the reviewing stations for final, expert resolution.

As described above, in various embodiments, each container will include and preferably be marked with a unique identifier. This identifier is also associated with each of the scanned images of that container, and with records used to track the container and its screening results. For example, all cargo can be coded with serial numbers that uniquely describe both the class of like items, and individual items within the class, such as by using a machine-readable code such as a barcode or an RFID tag. ULDs and other containers can also be uniquely coded/barcoded or otherwise coded, so that as serialized items are added to a container, a complete identification hierarchy is established.

Once the container is loaded on an aircraft or other transport such as a ship or truck, a complete manifest is automatically accumulated. An aircraft may contain many containers such as ULDs, each ULD may contain several classes of items, and each class is composed of individual, uniquely identified items. These unique identification numbers and hierarchy of identification allow the system to keep data paced with physical material flow. Tracking can be accomplished by scanning the bar code containing the unique identifying number at each point at which additional information is attributed to an item, or an item changes location or hierarchical status. The identifier is then used to update an associated record that can be maintained by any of the systems described herein, or by a centralized server that also can be implemented as a data processing system 200.

One benefit of this approach is that at the distributed scanning points, such as manufacturers or freight forwarders, the operator of the scan device is no longer required to be certified or have unique expertise. Scanning can therefore occur as material is prepared prior to ULD loading in a gradual process that matches the pace of ULD preparation. In some cases, the scanning equipment itself can simplified in that on site recognition and HMI functionality is removed from the scanner. This simplification, coupled with the relatively broad installation base, results in reduced cost per unit. The screening process is integrated with the normal processing and aggregation of cargo into ULDs destined for specific cities on wide-body aircraft. In this process, individual items can be digitally photographed as they are packed into boxes. The boxes are uniquely identified by barcode. The digital image for each type of item in a container can be electronically associated with the unique barcode for the container. In some embodiments, no more than one electronic image is captured for each type.

Once the container is sealed, the electronic manifest for the items it contains is associated with the container, and the container's barcode is scanned again as it is x-rayed. The x-ray image is associated with other electronic container information related to that container. The other electronic container information can include the unique identifier for the container, digital visible images for each type of item within the container, a manifest that describes the contents of the container, and a digital x-ray image of the sealed container.

This container information is forwarded to the reviewing stations or other centralized screening point for analysis by certified screeners in a controlled environment. For example, in one process, the screener is first showed the x-ray image of an individual container by the reviewing station. During examination and analysis of the x-ray image, the screener may need to see any or all of the digital visible images of the types of objects inside the container to be able to certify that the container can be loaded onto a passenger aircraft.

If the reviewing station receives a request from the screener (through the HMI) to view the digital visible images of the types of items in the container, the reviewing station can show the screener thumbnail images if more than one type of item is in the container, or the high resolution visible image if the container contains only a single type. When thumbnail images of multiple types are shown, the screener may select which image type to view in high resolution, and the reviewing station will display it.

If the screener is not satisfied, the screener may enter comments and indicate the features from the x-ray which cause concern, marking one or more of the contents as an exception, and effectively "reject" the container to preclude its loading into the container and onboard the aircraft, such as by using the exception indicator. The rejection, along with comments and identification of concern features, is included in the container data associated with the container's unique identification number. If the screener is satisfied, this result is included in the container data associated with the container's unique identification number. This updated information is available in the system, and when the container's barcode is read at the next processing step, such as container loading, the system will return the final status code to the operator.

As packaged goods are loaded into containers, the container is scanned, and the individual barcodes for constituent packaged goods are scanned. When container loading is complete, the container is sealed and its barcode is scanned, indicating completion of loading. When the sealed container is loaded unto a truck, its barcode can be scanned again, associating the items loaded into the container with the truck, and the status of the container's seal. When the truck unloads the container, the container's barcode is again scanned, informing the system of the change in status. This routine is extended through the container handling, from aircraft loading to container unloading after transport.

Overall security is enhanced through the processes described herein, in that a great deal of information is retained regarding the cargo that has been loaded on passenger aircraft or ship. This information would be critical in a forensic investigation or in the process of continually testing and monitoring the system. In addition the centralized screening architecture allows for continual training and evaluation of screeners. Images that include bona-fide threats may be introduced into the system, for which no actual container or item actually exists, may be introduced randomly to test and evaluate screeners in a way that is impractical to do in current systems.

Preferably, the containers are marked with scannable tags such as bar codes or RFID tags. In some embodiments, the system can also create a computerized content manifest is associated with the container, which lists item codes or descriptions making a security scan of each of the items in that container. This can be accomplished prior to loading the container, and associates the unique identifier of the container with unique identifiers of each item in the container.

Various other processes can be performed in various embodiments. For example, the system can associate security scan information with the code of that container in a database maintained by a one or more of the data processing systems described herein. Processes can include closing and sealing completed containers such that breach of the seal indicates that the container has been tampered with. Processes can include transporting the items by delivery of the container to one or more intermediate destinations before delivery to an unloading site at which the items are unloaded from the container. Processes can include inspecting the seal or breach on each such delivery and scanning the container code upon delivery to each intermediate destination and the unloading site providing scan results to a control computer, such as a central server 340, which associates the scan results with the code of the container and updates a data record for that container saving as part of the data record the location of the container and a status indication for that container when at that location.

Various steps of the processes described herein, unless otherwise specified, can be performed repeatedly, sequentially, concurrently, in a different order, or omitted entirely. Furthermore, the processes described above are not intended to be entirely distinct and separate processes unless so described, and various steps of different processes can be combined or performed in conjunction with each other. Similarly, various elements of the embodiments described above can be omitted from specific embodiments or combined with other embodiments.

Those skilled in the art will recognize that, for simplicity and clarity, the full structure and operation of all systems suitable for use with the present disclosure is not being depicted or described herein. Instead, only so much of the physical systems as is unique to the present disclosure or necessary for an understanding of the present disclosure is depicted and described. The remainder of the construction and operation of the systems disclosed herein may conform to any of the various current implementations and practices known in the art.

It is important to note that while the disclosure includes a description in the context of a fully functional system, those skilled in the art will appreciate that at least portions of the mechanism of the present disclosure are capable of being distributed in the form of a instructions contained within a machine-usable, computer-usable, or computer-readable medium in any of a variety of forms, and that the present disclosure applies equally regardless of the particular type of instruction or signal bearing medium or storage medium utilized to actually carry out the distribution. Examples of machine usable/readable or computer usable/readable mediums include: nonvolatile, hard-coded type mediums such as read only memories (ROMs) or erasable, electrically programmable read only memories (EEPROMs), and user-recordable type mediums such as floppy disks, hard disk drives and compact disk read only memories (CD-ROMs) or digital versatile disks (DVDs). In particular, computer readable mediums can include transitory and non-transitory mediums, unless otherwise limited in the claims appended hereto, having executable instructions that, when executed, cause one or more systems to perform processes as described herein.

Although an exemplary embodiment of the present disclosure has been described in detail, those skilled in the art will understand that various changes, substitutions, variations, and improvements disclosed herein may be made without departing from the spirit and scope of the disclosure in its broadest form.

None of the description in the present application should be read as implying that any particular element, step, or function is an essential element which must be included in the claim scope: the scope of patented subject matter is defined only by the allowed claims. Moreover, none of these claims are intended to invoke paragraph six of 35 USC §112 unless the exact words "means for" are followed by a participle.

What is claimed is:

1. A method performed by a plurality of interconnected data processing systems, comprising:
scanning a plurality of hems by a first data processing system to generate x-ray image data of the items, each of the plurality of items having a unique identifier;
performing a computer implemented image recognition process on the x-ray image data to identify the items;
interactively reviewing the x-ray image data with a human operator by a second data processing system, including displaying the x-ray image data to the human operator;
recording the result of the human operator's review;
determining, for each item, if the results from the computer implemented image recognition process and interactive review meet criteria for items that are exceptions that should not be shipped; and
storing an exception indicator for each item using the respective unique identifier.

2. The method of claim 1, further comprising:
photographing the plurality of items in human-visible light by the first data processing system to generate photographic image data of the item; and
interactively reviewing the x-ray image data and photographic image data with a human operator by a second data processing system, including displaying the x-ray image data and photographic image data to the human operator.

3. The method of claim 1, wherein only items that are not exceptions are loaded into a vehicle or shipping container.

4. The method of claim 1, wherein the second data processing system is geographically remote from the first data processing system.

5. The method of claim 1, wherein each of the plurality of items has a machine-readable tag with the unique identifier.

6. The method of claim 1, wherein the plurality of items is associated with a container, the container having a unique container identifier.

7. The method of claim 6, wherein unique identifier for each item is associated with the container unique identifier of the container.

8. A system configured to interact with a decentralized container checking device which is provided for local checking of a container, comprising:
a central data processing system remote from the container checking device;
a first interface configured to provide a data communication between the central data processing system and the decentralized container checking device, wherein the central data processing system processes in at least a first operating mode a data record captured by the decentralized container checking device corresponding to a transport procedure of the container; and
at least one second interface configured to make the data record processed by the central data processing system available for calling-up by a decentralized organization, wherein a security measure is initiated according to the data record.

9. The system of claim 8, wherein the data communication for transfer of the data record, the processing of the data record are performed as substantially real-time processes.

10. The system of claim 8, wherein the central data processing system is configured to analyze the data record for determining a security-related event which affects the transport procedure.

11. The system of claim 8, wherein the first interface is configured to create a data communication between the central data (processing system and the decentralized container checking device, which is operated in connection with an investigation of the container for the presence of non-permitted contents, and
wherein the investigation takes place in a security area protected according to security provisions preparatory to the transport procedures, and wherein the central data processing system, when operating in the first one operating mode, processes the data record with relation to a security-related event occurring during the investigation.

12. The system of claim 11, wherein the central data processing system processes the data record with relation to an event affecting the security area.

13. The system of claim 11, wherein the central data processing system processes the data record with relation to the contents of the container.

14. The system of claim 11, wherein the central data processing system is configured to make the data record available for calling-up during the presence of the container within the security area.

15. The system of claim 8, wherein the first interface is configured to communicate between the central data processing system and the decentralized container checking device, and wherein the decentralized container checking device is embodied as a mobile device accompanying the container during transit of the same.

16. The system of claim 15, wherein the central data processing system is configured in at least one operating mode to make the data record available to the decentralized organization during transit of the container.

17. A method, comprising:
checking a container using a decentralized container checking device to produce a data record;
transmitting the data record to a central check data processing device via an interface unit of the container checking device;
processing the data record from the check data processing device with regard to a transport procedure of the container; and
making the data record available for retrieval by a decentralized organization, wherein a security measure is initiated according to the data record.

18. The method of claim 17, wherein the container is checked for the presence of non-permitted contents using an investigation device of the decentralized container checking device in a security area protected according to security provisions, the security area is monitored using a monitoring device, and data records from the investigation device and the monitoring device are transmitted to the central check data processing device.

19. The method of claim 17, wherein the container is checked using a mobile checking device accompanying the container during transit, and a data record of the checking device is transmitted to the central check data processing device.

* * * * *